United States Patent
Efstathiou et al.

(10) Patent No.: US 9,345,669 B2
(45) Date of Patent: May 24, 2016

(54) BIODEGRADABLE NATURAL FILMS BASED ON CO-PRODUCTS DERIVED FROM INDUSTRIAL-SCALE SEED-TREATMENT PROCESSES

(75) Inventors: Theo Efstathiou, Pace (FR); Jean-Luc Audic, Montfort sur Meu (FR); Thomas Divers, Saint-Etienne (FR)

(73) Assignee: Sojasun Technologies, Moyal sur Vilaine (FR)

( * ) Notice: Subject to any disclaimer, the term of this patent is extended or adjusted under 35 U.S.C. 154(b) by 121 days.

(21) Appl. No.: 13/990,151

(22) PCT Filed: Nov. 28, 2011

(86) PCT No.: PCT/EP2011/071196
§ 371 (c)(1),
(2), (4) Date: Aug. 2, 2013

(87) PCT Pub. No.: WO2012/072587
PCT Pub. Date: Jun. 7, 2012

(65) Prior Publication Data
US 2014/0008264 A1    Jan. 9, 2014

(51) Int. Cl.
| | |
|---|---|
| *A61K 36/48* | (2006.01) |
| *A61K 9/70* | (2006.01) |
| *C08J 5/18* | (2006.01) |
| *A23L 1/00* | (2006.01) |
| *A61K 45/06* | (2006.01) |

(Continued)

(52) U.S. Cl.
CPC ............... *A61K 9/7007* (2013.01); *A23L 1/00* (2013.01); *A61K 9/006* (2013.01); *A61K 31/00* (2013.01); *A61K 31/352* (2013.01); *A61K 35/741* (2013.01); *A61K 36/48* (2013.01); *A61K 45/06* (2013.01); *A61K 47/46* (2013.01); *C08J 5/18* (2013.01); *C08L 89/04* (2013.01); *C08J 2399/00* (2013.01)

(58) Field of Classification Search
CPC ....................................................... A61K 36/48
USPC ............................................................ 424/757
See application file for complete search history.

(56) References Cited

U.S. PATENT DOCUMENTS

| | | | | |
|---|---|---|---|---|
| 4,664,930 | A | * | 5/1987 | Moriya .......................... 426/573 |
| 4,911,945 | A | * | 3/1990 | Kawasaki et al. ............. 426/656 |

(Continued)

FOREIGN PATENT DOCUMENTS

| | | |
|---|---|---|
| EP | 1132084 A1 | 9/2001 |
| GB | 1510999 A | 5/1978 |

(Continued)

OTHER PUBLICATIONS

Cho et al. Lebensmittel-Wissenschaft und -Technologie. 2004. vol. 37, No. 8, pp. 833-839.*

(Continued)

*Primary Examiner* — Chris R Tate
(74) *Attorney, Agent, or Firm* — Thomas Horstemeyer, LLP

(57) ABSTRACT

A biodegradable film (4) characterized in that it is prepared from at least one co-product derived from a soya bean-processing process aimed at obtaining soya-based final products by ultrafiltration, said co-product being selected from the group comprising the okara and the permeate. Such a film can be used as a food or pharmaceutical film, in particular for preparing a product for topical administration (1) of a pharmaceutical active ingredient, such as oestrogens.

14 Claims, 5 Drawing Sheets

(51) Int. Cl.
*A61K 47/46* (2006.01)
*A61K 31/00* (2006.01)
*A61K 31/352* (2006.01)
*A61K 9/00* (2006.01)
*C08L 89/04* (2006.01)
*A61K 35/741* (2015.01)

(56) References Cited

U.S. PATENT DOCUMENTS

| | | | | |
|---|---|---|---|---|
| 6,004,616 | A * | 12/1999 | Maeda et al. | A23G 4/068 106/163.01 |
| 6,379,726 | B1 * | 4/2002 | Tomasula | 426/89 |
| 2004/0107840 | A1 * | 6/2004 | Moriyama et al. | 99/275 |
| 2006/0041036 | A1 * | 2/2006 | Mohanty et al. | 524/9 |
| 2007/0218164 | A1 * | 9/2007 | Stojanovic | 426/2 |
| 2007/0292487 | A1 * | 12/2007 | Loewy et al. | 424/443 |
| 2011/0027364 | A1 * | 2/2011 | Ambrosio et al. | 424/484 |
| 2011/0287162 | A1 * | 11/2011 | Gottemoller | 426/634 |

FOREIGN PATENT DOCUMENTS

| | | | |
|---|---|---|---|
| JP | 2000281917 | | 10/2000 |
| WO | WO 2009/100593 | * | 8/2009 |

OTHER PUBLICATIONS

Wang et al. JAOCS. 1998. vol. 75, No. 3, pp. 337-341.*
The International Search Report and Written Opinion dated Feb. 1, 2012.
The International Preliminary Report on Patentability dated Jun. 4, 2013.
Database WPI Week Feb. 2001 Thomson Scientific, London, GB, AN 2001-011149, XP002642065.
Monedero, et al., "Effect of Calcium and Sodium Caseinates on Physical Characteristics of Soy Protein Isolate-Lipid Films," Journal of Food Enginnering, vol. 97, Oct. 20, 2009, pp. 228-234.
Su, et al., "Properties Stability and Biodegradation Behaviors of Soy Protein Isolate/Poly (Vinyl Alcohol) Blend Films," Polymer Degradation and Stability, vol. 95, Apr. 14, 2010, pp. 1226-1237.

* cited by examiner

BIODEGRADABLE NATURAL FILMS BASED ON CO-PRODUCTS DERIVED FROM INDUSTRIAL-SCALE SEED-TREATMENT PROCESSES

CROSS REFERENCE TO RELATED APPLICATION

This application claims priority to PCT Application entitled "Biodegradable Natural Films Based on Co-Products Derived from Industrial-Scale Seed-Treatment Processes," having serial number PCT/EP2011/071196, filed on 28 Nov. 2011, which claims priority to and benefit of French Patent Application No. 1059871, filed on 29 Nov. 2010, which is incorporated by reference in its entirety.

The invention pertains to the field of biodegradable materials and more specifically to that of films made out of natural products.

Issues related to ecology and the protection of the environment are increasingly coming to the fore and being integrated into industrial policies, especially in the chemical industry sector.

"Clean chemistry" or "green chemistry" tends to reduce or even eliminate the use and production of dangerous substances in the designing, manufacture and application of chemical products.

Three fields can be singled out:
the designing of innovative technologies to ensure availability and use of renewable energies,
the development of renewable resources and products derived therefrom,
the creation of technologies that do not cause pollution.

One non-negligible source of pollution results from the manufacture and use of plastic films, especially plastic packaging and bags.

Conventional plastic films, generally based on vinyl polymers, account for 4% of petroleum consumption (petroleum being a non-renewable fossil raw material) and amount to more than 1000 KT/year of wastes of which only 20% are recycled.

In this context, the development of natural biodegradable films represents a major challenge.

Several industrial-scale methods for making starch-based film have been obtained with success. Starch is a carbohydrate reserve produced and used by the higher forms of plant life to store energy. It is found in the reserve organs of plants, seeds (especially cereals and legumes), roots, tubers and rhizomes (potato, sweet potato, cassava, etc). At the industrial level, it is especially maize and potatoes that are used. Starch is not only a renewable raw material but also a non-toxic and entirely natural material.

However, these films have two major drawbacks:
their degradation is slow, of the order of some months to some years,
they continue to incorporate a limited but non-negligible percentage of non-biodegradable compounds in their composition and these compounds are liable to be located in the soil after the degradation of the film and could prove to be very difficult to recover.

The goal of the present invention is to provide a natural and biodegradable film that does not have the drawbacks of the prior-art films.

In particular, one of the goals of the invention is to provide a natural and biodegradable film that does not incorporate non-biodegradable compounds into its composition.

It is another goal of the invention to propose a film of this kind, the degradation of which is improved as compared with prior-art films, i.e. a film whose degradation is far more extensive and is quicker.

It is another goal of the invention to propose a film of this kind that is a relatively low-cost film and complies with the requirements of "clean chemistry".

It is also a goal of the present invention, in certain of its embodiments, to provide biodegradable films for use in the pharmaceutical or medical fields.

The invention pertains to a biodegradable film characterized in that it is made out of at least one co-product derived from a process for treating seeds of plants known as cereal plants and/or leguminous plants and/or oilseed plants.

The term "co-product" is understood to mean products other than the main product or the main products obtained by the industrial process in question. Such "co-products" are put to little good use or no good use at all in the prior art.

The term "biodegradable" is understood to mean that the film according to the invention is a film which can be degraded naturally by living organisms such as for example bacteria. This degradation can be obtained by a step of fragmentation of the film.

The films according to the present invention are of natural origin inasmuch as the co-products that go into their composition have not undergone any chemical treatment and inasmuch as any products other than said co-products that go into this composition are also products of plant or animal origin that have undergone no chemical treatment.

Said seeds of plants known as cereal plants and/or leguminous plants and/or oilseed plants could include wheat grains, barley grains, rice grains, corn grains, rye grains, oats, triticale, linseed, hemp seeds, rapeseed, sunflower seeds, cotton seeds, peanuts, mustard seeds and broccoli seeds.

The leguminous seeds could include soybeans, buckwheat seeds, chickpeas, beans, cocoa beans, lentils and pumpkin seeds.

The seeds from the oilseed plants could for example be linseed, hemp seeds, rapeseed, sunflower seeds, peanuts, soybeans, sesame seeds, walnuts and almonds.

The use of co-products and not main products such as seeds and flour to manufacture film according to the invention is fully acceptable from the ethical viewpoint. It moreover complies with the new requirements of sustainable development.

Preferably, the film is made out of a co-product derived from a process for treating soybeans.

There are various known industrial-scale processes in the prior art for treating soybeans that lead to various co-products.

Thus soy milk, which is in fact a juice also known to those skilled in the art by its Japanese name "tonyu", is obtained by pressing soybeans.

According to the classic industrial process for treating such soybeans to obtain soy milk, these soybeans are first of all husked in order to remove their skins.

The kernels thus obtained are rehydrated with water (the percentage by weight of soybean used relative to water is generally 10%) and then the beans are crushed and the obtained crushed product is centrifuged to give, on the one hand, soy milk and on the other hand a residual pulp also known as "okara".

This soy milk can undergo membrane ultrafiltration following which on the one hand, a retentate and, on the other hand, a permeate, are obtained.

The industrial-scale process for treating soybeans to obtain soy milk therefore results in two by-products, namely skins and okara. When this "soy milk" is ultra-filtered to make yoghurt, a supplementary co-product, namely permeate, is obtained.

There are also known ways of extracting soy oil and soy protein from soybeans. The soy skins constitute what is left of the bean after such extraction. These skins therefore constitute a co-product from such processes of extraction from soybeans.

In the prior art, the co-products derived from the industrial treatment of soybeans, namely the skins, the okara and the permeate are hardly exploited or not exploited at all.

According to the invention, the co-product or co-products derived from the process of treating soy beans to make a biodegradable natural film are preferably chosen from the group constituted by okara and permeate from soy milk filtration.

It will be noted that okara could be used in the form of dry okara, i.e. containing at least 95% by mass of dry extract or in the form of wet okara, i.e. containing between 20% and 25% by mass of dry extract.

The biodegradable natural films according to the invention can show properties at least equal to those of the prior-art films, especially in terms of mechanical strength and non-toxicity.

In a totally unexpected way, the inventors have demonstrated that, in addition, the use of co-products derived from an industrial-scale process for treating soybeans can be used to obtain biodegradable films with a speed and efficiency of degradation that are improved over those of the prior-art films.

According to one particular aspect, the natural and biodegradable film according to the invention is a food-grade film.

The term food-grade film is understood to mean any agri-food-grade film intended for:
 the protection of items such as chocolate, biscuits, eggs, fruit, vegetables, dry groceries, etc;
 the composition of materials for carrying food such as cans, bottles, trays, jars, etc;
 the making of ground-covering or mulching films. After the harvesting of fruit and/or vegetables, the film is mixed with the earth and then serves as fertilizer.

According to another aspect, the natural and biodegradable film of the invention is a packaging film.

According to yet another aspect, the film according to the invention is an excipient with a solid galenic form for the application of an active ingredient.

The term "solid galenic form" refers not only to the film itself but to any individual form given to the active ingredient or ingredients and the excipient or excipients in order to constitute a medicine. It corresponds to the physical appearance of the medicine as used by the patient. Such forms include: sticks, tablets, soft capsules, coated tablets, hard capsules and pills. At present, the excipient most used for capsules is either gelatin (animal protein) or cellulose (polysaccharide of plant origin). To obtain these galenic forms, the film according to the invention will be quite simply wound on itself.

According to yet another particularly worthwhile aspect, the natural and biodegradable film according to the invention is a film for pharmaceutical or medicinal use for the topical application of at least one active ingredient.

According to one valuable alternative, the film according to the invention is a film for gynecological use.

Preferably, the film according to the invention comprises a film-forming agent in its composition.

Advantageously, said film-forming agent is chosen from the group constituted by caseinates and protein fractions derived from processes for manufacturing milk products. The term "caseinates" is understood to mean chiefly: sodium caseinate, potassium caseinate, calcium caseinate and magnesium caseinate. These products of natural origin are indeed easily available.

According to one variant, the film according to the invention comprises at least one plasticizer in its composition.

Preferably, said plasticizer is glycerol. This compound has the advantage of being biocompatible.

Advantageously, the film according to the invention includes the following in its composition, at least when is used for pharmaceutical or medicinal purposes:
 0% to 40% by mass of permeate;
 0% to 20% by mass of okara;
 5% to 60% by mass of plasticizer;
 20% to 90% by mass of film-forming agent;
 0% to 20% by mass of water.

The invention also pertains to a product for administering at least one active ingredient characterized in that it comprises at least one film for pharmaceutical or medicinal use as described here above and at least one active ingredient associated with said film. The association of said at least one active ingredient with the film can be applied by different techniques such as surface deposition, impregnation and incorporation into the initial mixture. Such a film can be applied to a mucous membrane.

According to one variant, said film with which said at least one active ingredient is associated is intended for application to the lips or to the inside of the mouth.

According to another variant, said film with which at least one active ingredient is associated is intended for application to the vulva or in the vagina.

The consequences of the post-menopausal ageing of the genito-urinary system occur most frequently only several years after the onset of menopause. This is the reason why the pathologies resulting from them are quite poorly known to the public and are relatively poorly treated by the medical profession.

Local estrogen deficiency leads to well-known physical/chemical modifications of the muscular tissues of the perineum, the vaginal epithelial tissues, the urethra and the bladder leading to crippling pathologies often associated with:
 vaginal dryness and atrophy possibly leading to pain and infection;
 modifications of the vaginal bacterial flora leading to repeated urinary infection (14% of women being affected towards the age of 65, and 25% towards the age of 85);
 stress urinary incontinence and overactive bladder incontinence (frequency and urgency of micturition);
 prolapse etc.;

In France, it is estimated that 5 million women suffer from urinary incontinence (200 million in the world). 15 to 20% of women after 60 suffer from urinary incontinence in the form of either stress incontinence or overactive bladder incontinence or mixed incontinence.

Local estrogen replacement therapy makes it possible to prevent, improve or even heal this condition in most women concerned either alone by continuous maintenance therapy or in association with other active ingredients such as for example anti-cholinergic active ingredients.

Several replacement estrogens are known and have the same therapeutic efficacy. These include especially estriol, estradiol, promestriene. However, there are many questions about the relationship between the use of replacement estrogens after menopause and the onset of breast cancer. These questions hamper the prescription of estrogen as a preventive measure or in the treatment of post-menopausal ageing of the genito-urinary system. Thus, the manufacturer does not recommend the use of promestriene (Colpotrophine®) vaginally for patients with antecedents of breast cancer. However, phyto-estrogens are not contraindicated. These phyto-estrogens, on the contrary, are thought to have a preventive effect in breast cancer. No study at present has demonstrated any definite link between the use of replacement phyto-estrogens and the development of breast cancer.

The use of orally administered replacement estrogens does not have a convincing effect on different forms of incontinence. On the contrary, certain studies show that such use can aggravate this condition.

There are vaginal creams at present. This mode of local administration improves the control and targeting of the effects of estrogen but is difficult to apply.

The invention therefore proposes a product for administering at least one active ingredient including a film made out of at least one co-product derived from a process for treating soybeans intended for application to the vulva or in the vagina wherein said at least one active agent is an estrogen or a pseudo-estrogen.

Advantageously, said active ingredient is contained in an extract of soybeans. Such an extract of soybeans preferably includes a mixture of daidzin and genistin. These compounds are isoflavones and constitute pseudo-estrogens of plant origin or phyto-estrogens.

According to one variant, the product for administering, including a film intended for application to the vulva or in the vagina, comprises a second ingredient which is preferably a probiotic ingredient.

As indicated here above, during menopause, estrogen deficiency induces trophic disorders which are responsible for pathological symptoms. The vaginal flora gets modified, the lactobacilli diminish by 50%, the anaerobic bacteria predominate owing to peroxidation processes induced by infections related to the diminishing of the Döderlein flora. This estrogen deficiency also leads to an increase in bacterial adherence. In addition, it favors the rise of the pH factor and is a cause of numerous disorders such as nycturia, urinary frequency, incontinence, urinary infections, etc.

It can thus be seen that a direct addition of probiotics into the vagina can help restore the bacterial equilibrium of the vaginal flora and thus prevent the development of pathologies.

According to one variant, a product for administering according to the invention comprises two distinct compartments shut by at least one lid, one of said two compartments containing said film associated with said first active ingredient and the other of said two compartments containing at least one second active ingredient, said two compartments being intended to be folded one on top of the other after removal of said lid so that the second active principle is deposited on the film.

The film can be applied with the fingers or using a vaginal applicator such as the applicators described especially in the patent applications FR 2 872 702 A3, US 2003/229328 A1, US 2005/171463 A1, US 2005/197615 A1, US 2005/273039 A1 and the patents GB 2 412 321 B1 and U.S. Pat. No. 7,591,808 B2. When an applicator is used, the film will advantageously have a cylindrical shape or the shape of a glove finger, such shapes being efficient supports for adding estrogens as well as other active ingredients especially probiotics. Cylindrical films or films shaped like gloved fingers are placed in an applicator so that they can be more easily delivered to the zone of interest. Preferably, the applicators used will be a disposable applicator.

The invention, as well as the advantages that it procures, will be more easily understood from the following description of non-exhaustive examples of the making of films and of products for administering active ingredients including such films according to the invention, made with reference to the appended figures, of which:

EXAMPLES OF BIODEGRADABLE FILMS ACCORDING TO THE INVENTION

Figure 1:
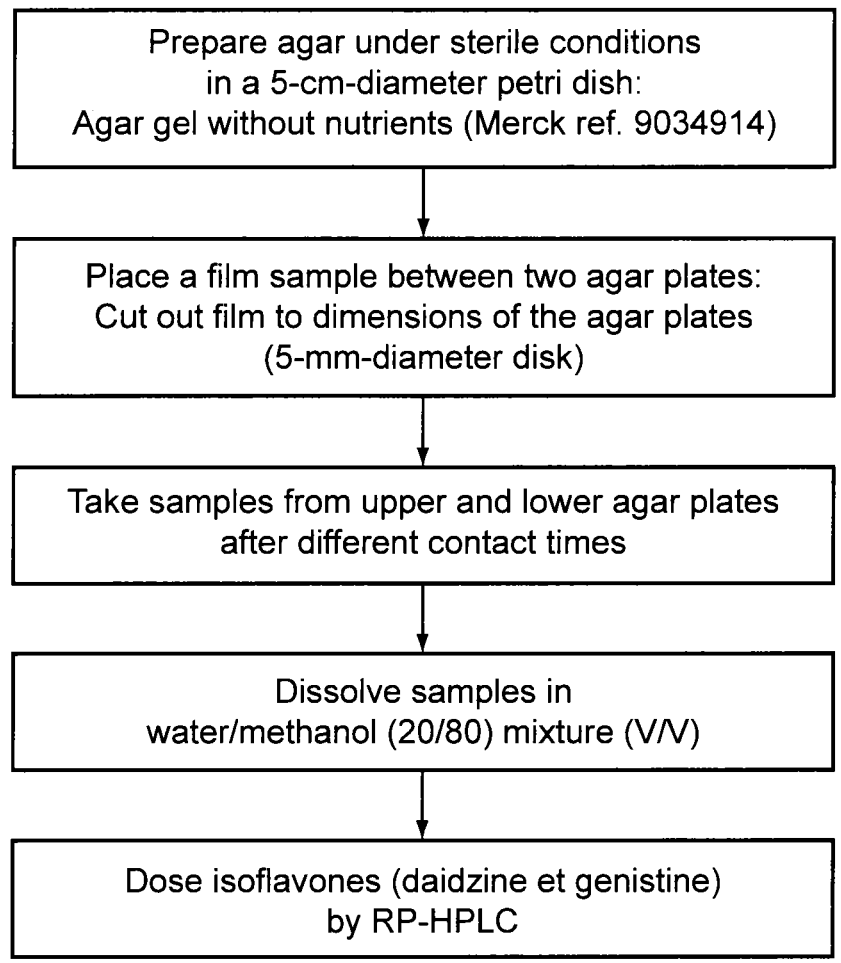
FIG. 1 is a flowchart pertaining to the protocol for evaluating the diffusion of isoflavones made out of films according to the invention towards a matrix simulating the vaginal mucous membrane.
Figure 6:
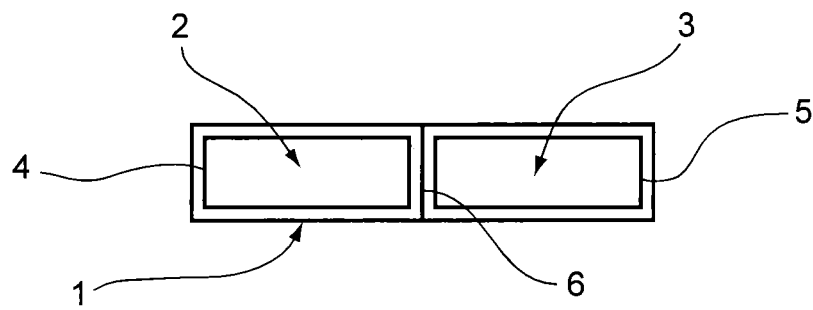
FIG. 6 represents an embodiment of a product for administering including a biodegradable film impregnated with active ingredients for pharmaceutical use according to the invention.

Different biodegradable films according to the present invention are made with the casting process described here below.

For each formulation of a film, described in detail in table 1 here below, different fractions of co-products derived from the treatment of soybeans for obtaining soy-based finished products, the permeate fraction and the okara fraction were mixed with a fraction of a film-forming agent and a fraction of plasticizer.

In the context of the present embodiment, this mixture was poured onto a polystyrene (PS) support in the shape of a rectangular vessel. After evaporation of the excess water, the films obtained were de-molded and then enclosed in a receptacle in which the atmosphere was maintained at a relative humidity of 53% through a solution saturated with magnesium nitrate ($Mg(NO_3)_2$). The films were then cut out into test specimens capable of undergoing different mechanical tests.

It can be noted that, for industrial-scale application, it could planned to make the mixture by means of an industrial-scale internal mixer such as a mixer bearing the trade name "HAAKE Polydrive". Such a piece of equipment, which is commercially available, comprises a mixer chamber in which there are two counter-rotating helical rotors. The mixture can then be thermo-pressed in a hydraulic heat press such as the one commercially available by the trade name "CARVER3860-416".

TABLE 1

| Formulation n° | Permeate (% by weight) | Okara (% by weight) | Film-forming agent (% by weight) | Total T (permeate + okara + film-forming agent) | Plasticizer (% by weight relative to total T) |
|---|---|---|---|---|---|
| 0 | 60 | 0 | 40 | 100 | 10 |
| 1 | 30 | 30 | 40 | 100 | 20 |
| 2 | 20 | 20 | 60 | 100 | 20 |
| 3 | 20 | 30 | 50 | 100 | 20 |
| 4 | 30 | 20 | 50 | 100 | 20 |
| 5 | 30 | 30 | 40 | 100 | 20 |
| 6 | 30 | 30 | 40 | 100 | 30 |

In these formulations, the film-forming agent is sodium caseinate (NaCas), except for the formulation 3 where it is buttermilk concentrate (BMC) powder and glycerol plasticizer (gly).

Each fraction of the formulations used is characterized in Table 2 here below.

TABLE 2

| Fraction | Humidity (% by mass) | Proteins (% by mass) | Lipids (% by mass) | Minerals (% by mass) | Sugars (% by mass) | Other (% by mass) |
|---|---|---|---|---|---|---|
| Okara | 4 | 30 | 15 | 4 | 0.5 | 46.5 (fibers) |
| Permeate | 4 | 10 | 0 | 9 | 45 | 32 (ash) |
| NaCas | 6 | 90 | 0.5 | 3.5 | — | — |

Five specimens of the film according to the composition 0, 10 cm wide, 1.5 cm wide and about 200 µm wide were cut out in order to measure their mechanical properties by tensile tests. The tensile machine used is an MTS Synergie RT 1000 machine with a 250 N load cell. The specimens were all kept at a humidity level of 53% before the tensile tests were performed.

The results shown in table 3 below are averages obtained for the five specimens:

TABLE 3

| Mechanical property | Results (average value) |
|---|---|
| Modulus of elasticity E (MPa) | 55 |
| Breaking stress $\square_r$ (MPa) | 1.8 |
| Elongation at breaking point $\square_r \square \square \square$ %) | 70 |

These tests show that the permeate fraction enables the films to be given good mechanical properties.

The fiber-rich okara (60% in the dry product) gives the film a rigid and brittle character. This is sought for pharmaceutical films to enable them to disintegrate.

Examples of Products for Administering Active Ingredients According to the Present Invention The films according to the present invention meeting the formulations 1 to 6 described here above were associated with an extract obtained from soybeans. The extract is incorporated directly into the mixture so that its content is 4.2% by mass. This extract has the particular feature of being rich in isoflavones and especially having high daidzin and genistin content.

These isoflavones have pseudo-estrogen properties and can therefore be used to combat estrogen deficiency appearing during menopause. In this respect, they are an active ingredient. They come in two forms in the soybean extract in question, namely in glycosylated form (daidzin and genistin) and in aglycone form (daidzein and genistein). Table 4 shows the structures of these compounds.

TABLE 4

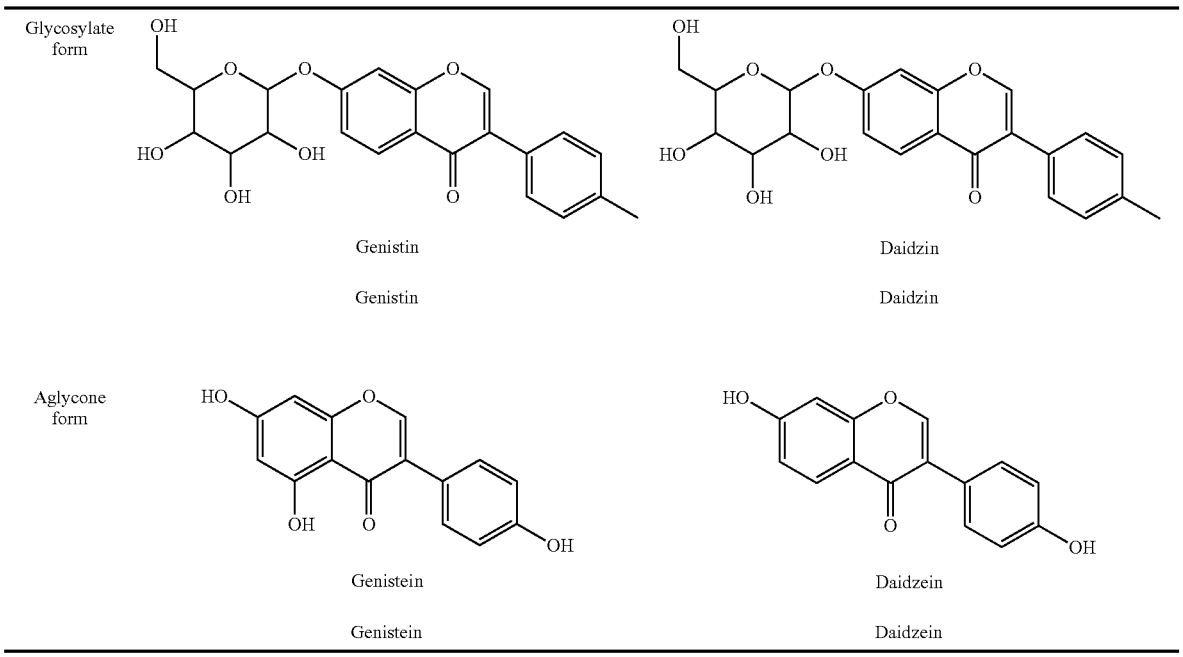

It can be noted that the aglycone form is the only form that can pass into the blood-stream and is therefore the only form that can be directly assimilated by the organism. However, the glycosylate form can be hydrolyzed in aglycone form by the vaginal flora. This is very valuable for the gradual diffusion of the active ingredient. The precise composition of the soybean extract in question is given in the following table 5 below.

TABLE 5

| Constituent element | Proportion by weight |
|---|---|
| Isoflavones of which: | Min. 40% |
| Daidzin | 17.5% |
| Genistin | 16.3% |
| Other natural constituents of soy including: | 40-50% |
| Proteins | Max. 12% |
| Fats | Max. 1% |
| Heavy metals | Max. 5 ppm |
| Moisture | Max. 7% |

The films associated with this isoflavone-rich extract form products for administering active ingredients contained in this extract to the vaginal mucous membrane.

The tests explained here below show the possible use of films according to the invention for making products for administering active ingredients by diffusion of these ingredients from the film towards the vaginal mucous membrane.

In these tests, in order to model the vaginal mucous membrane, an agar plate with an Agar concentration of 30 g/l was used.

The general protocol of study of the diffusion in the matrix is given in FIG. 1.

Figure 2:
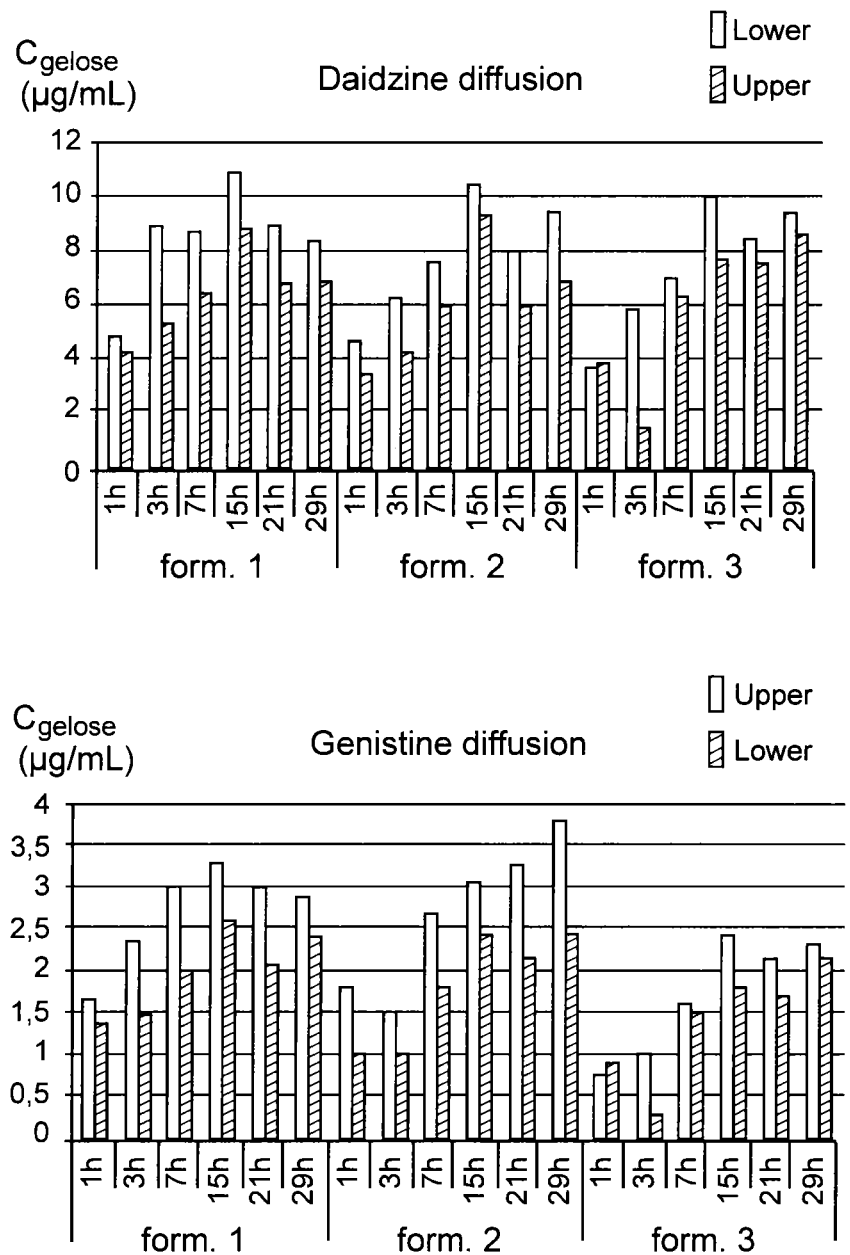
FIG. 2 represents two graphs showing the diffusion of isoflavones from films according to the invention into the matrix.

The diffusion of daidzin and genistin in the lower agar plate and the upper agar plate was studied with films complying with the formulations 1, 2 and 3 described here above. The results of this study are indicated in the two graphs of FIG. 2.

As can be seen in these graphs, the progress of the concentration of daidzin in gelose as a function of time is similar to that of genistin.

In addition, the concentration of daidzine in gelose under equilibrium is about 10 µg/mL while that of genistin is only 3.5 µg/mL. Since the proportion of each of these two isoflavones is similar in the isoflavone-concentrated commercially available product (175% for daidzin and 16.3% for genistin), it demonstrates the fact that daidzin is diffused more easily than genistin in gelose.

Figure 3:
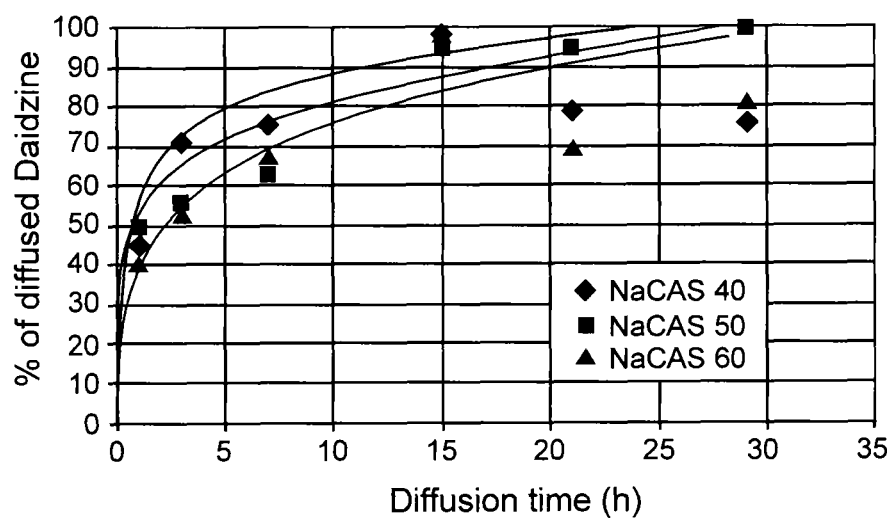
FIG. 3 represents two graphs showing the influence of the rate of film-forming agents of the films according to the invention in the diffusion of isoflavones into the matrix.
Figure 3:
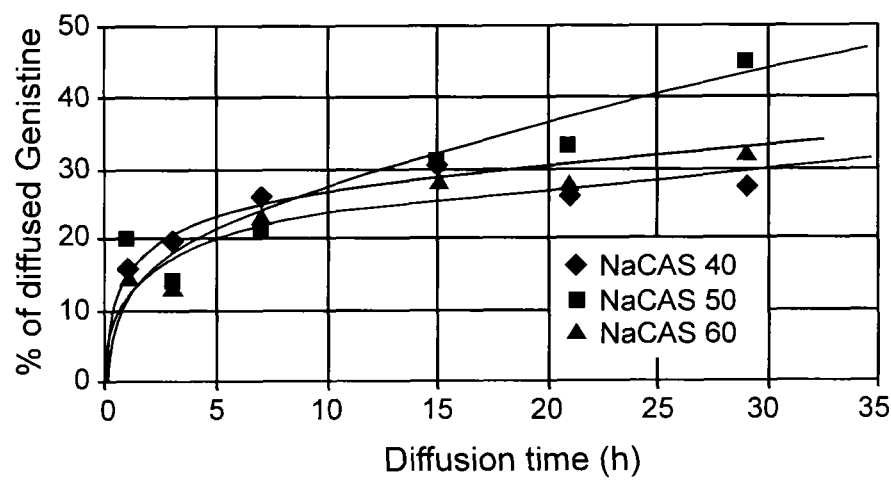

The influence of the proportion by weight of film-forming agent (sodium caseinate (NaCAS)) in films according to the invention meeting the formulations 5, 2 and 4 described here above on the diffusion of daidzin (a) and genistin (b) has also been studied. The results of this study are indicated in the two graphs shown in FIG. 3 in which the concentration in isoflavones diffused has been related in terms of percentage to the case where the entire active ingredient would have been diffused.

The interpretation of these two graphs makes it possible to conclude that the profile of diffusion of the two isoflavones in the different films according to the invention is similar. It would appear however, that the greater the increase in the proportion of film-forming agent in the formulation, the greater the reduction in the kinetics of diffusion. This result is consistent inasmuch as a greater protein fraction implies a more pronounced cohesive character of the film thus making the diffusion probably more difficult. These graphs also indicate that the speed of diffusion remains relatively high, especially in the case of daidzin, where more than 90% of the isoflavone was diffused after 24 hours of contact. As mentioned in a previous paragraph, genistin diffuses more slowly. Thus, after 24 hours, only 30-45% of the isoflavone had diffused towards the gelose according to the proportion in sodium caseinate in the formulation. However, after 30 hours, the state of equilibrium has still not been reached since the curve continued to rise. This behavior can be valuable for a more gradual release of this active ingredient.

The influence of a hydrophobic coating on the surface of the film was also studied.

The hydrophobic agent chosen for this study is soy lecithin. A suspension of this compound was also prepared using 5 g of soy lecithin powder mixed with 10 mL of ultra-pure water. The films complying with the formulations 1 and 2 were then coated with this suspension (on the upper and lower faces) and then placed on gelose in order to carry out migration tests.

Figure 4:
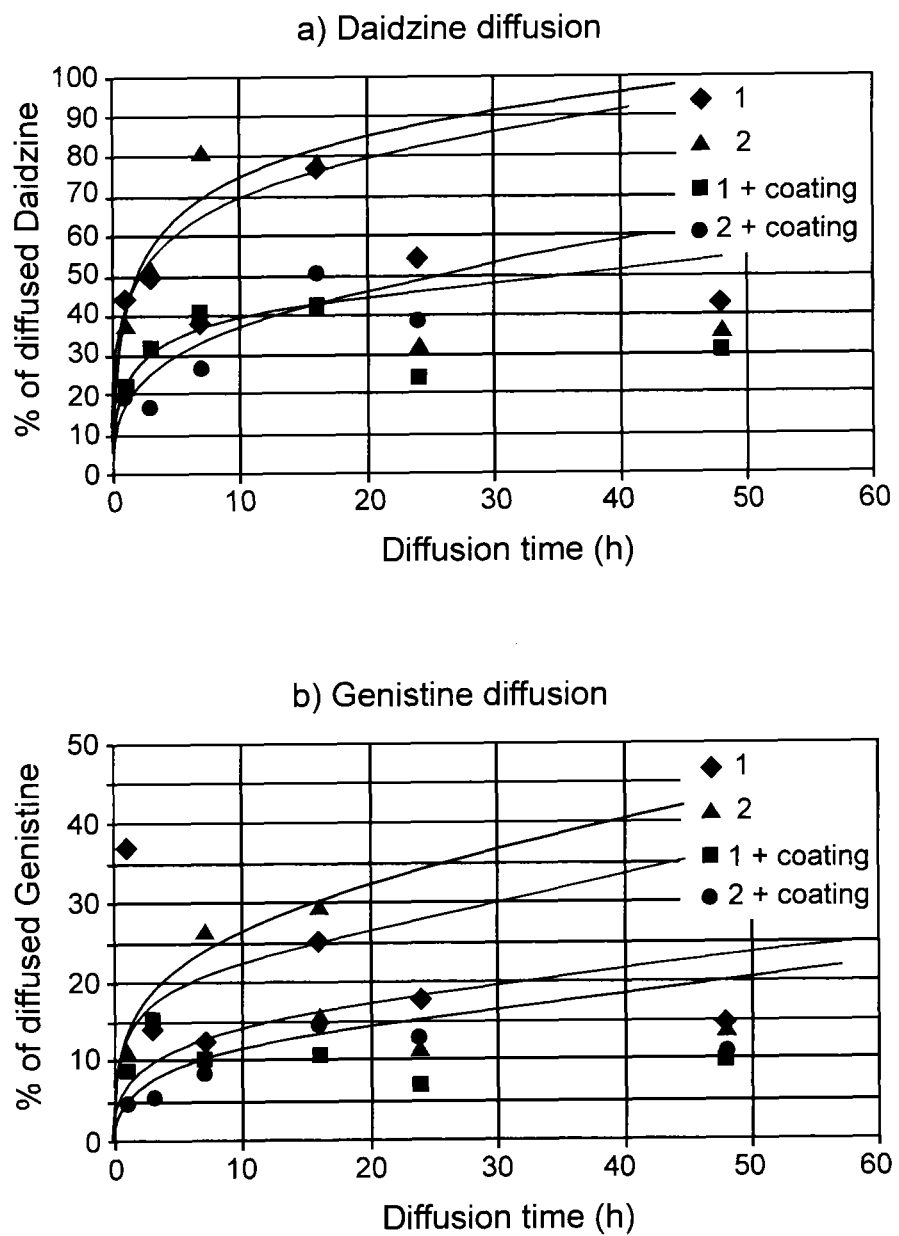
FIG. 4 represents two graphs showing the influence of the rate of hydrophobic coating of the films according to the invention in the diffusion of isoflavones into the matrix.

The results of this study are given in the two graphs in FIG. 4 which indicate the profiles of diffusion of the isoflavones with and without hydrophobic coating.

The profile of diffusion of the two isoflavones is again similar here. It can also be noted that the kinetics of diffusion of genistin is still slower. Indeed, after 48 hours of contact, about 90% of the daidzin had diffused in the gelose for both formulations without coating, whereas only 40% of the genistin had diffused after the same contact time (respectively 40% and 20% for daidzin and genistin in the case of formulations with soy lecithin coating).

The presence of a soy lecithin coating on the surface of the film significantly reduces the quantity of active ingredient being diffused towards the gelose and this is the case both for daidzin and for genistin. Indeed, the quantities of daidzin and genistin diffused in the gelose after 48 hours respectively go from 90% to 40% and from 40% to 20%. This may have two causes. Firstly, the fact of adding an additional layer increases the path to be travelled and therefore the duration of diffusion. Secondly, the hydrophobic nature of this layer gives rise to repellent interactions with the highly polar isoflavones, thus reducing their speed of migration towards the gelose. Furthermore, this hydrophobic layer limits the infiltration of water molecules into the film and therefore the extraction of isoflavones by water.

It must also be noted that the comparison of the two formulations studied herein leads to the same conclusion as in the above paragraph, namely that a greater fraction of film-forming agent (NaCAS) in the formulation, generating a more cohesive material reduces the speed of diffusion for the films without hydrophobic coating. By contrast, for the formulations with a hydrophobic coating, this observation is less pronounced, probably because of the repellent interactions above-mentioned.

Finally, the influence of the proportion by weight of plasticizer (glycerol (gly)) in the films of the invention on the diffusion of daidzin (a) and genistin (b) was also studied.

Two rates of plasticization were examined, corresponding to the formulations 4 and 5 of the films according to the invention described here above.

Figure 5:
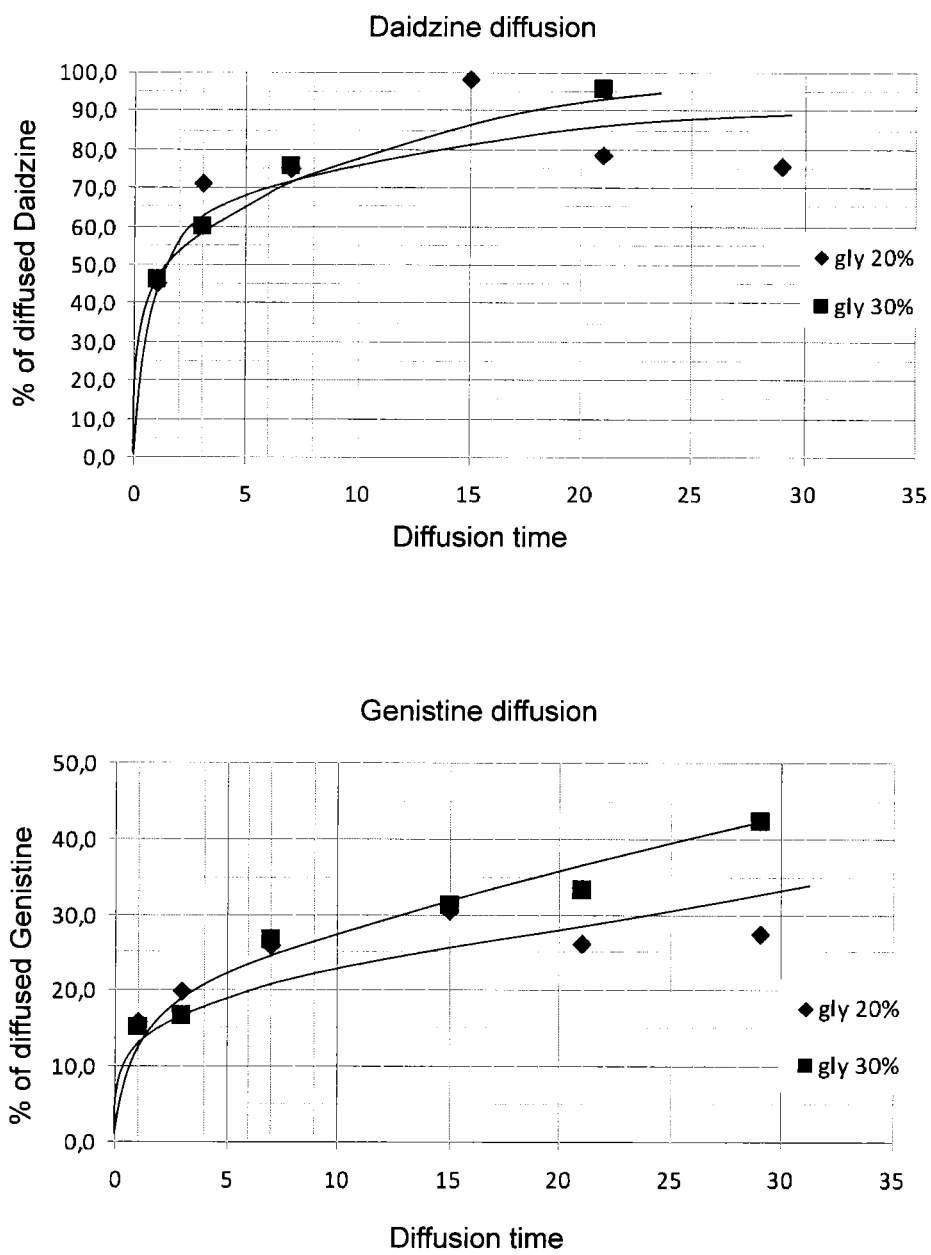
FIG. 5 represents two graphs expressing the influence of the rate of plasticizer agent according to the invention in the diffusion of isoflavones into the matrix.

The results of this study are indicated in the two graphs shown in FIG. 5.

The interpretation of these graphs indicates that genistin is diffused always more slowly than daidzin (40% of the totality of the genistin present initially in the film having migrated after 30 hours of contact as against 90% to 100% for daidzin). A high rate of plasticization gives rise to a slight increase in the speed of diffusion of the active ingredients as well as the quantity diffused. Indeed, for the glycerol rates of 30% by mass, almost 100% of the daidzin and 45% of the genistin are diffused after 30 hours as against 90% and 35% for daidzin and genistin respectively for a plasticization rate of 20%. This result is consistent in the sense that a higher rate of plasticization implies greater chain mobility, thus favoring the diffusion of isoflavones.

Here below, we describe another embodiment of a product for administering active ingredients including a biodegradable film according to the present invention.

In this embodiment, the product 1 for administering phyto-estrogens and probiotics according to the present invention comprises two distinct compartments 2, 3 covered by a transparent blister. These two compartments 2, 3 are made of plastic materials of rectangular shape and small thickness.

The first compartment 2 contains, under neutral atmosphere, a pharmaceutical film 4 according to the invention made out of a co-product derived from an industrial process for treating soybean and impregnated with a first active ingredient as described here above.

The second compartment 3 contains, under neutral atmosphere, a second active ingredient 5 in the form of a lyophilisate having the appearance of a powder.

In the embodiment presented, the first active ingredient consists of phyto-estrogens in aglycone form constituted by isoflavones derived from soybeans, in glucosylate form or still in aglycone form, its content being 10 to 100 mg/dose/day, preferably a content of 70 mg/dose/day.

The second active ingredient for its part is constituted by lyophilized probiotics, namely *Lactobacillus acidophilus* bacteria, the content of which is 20 mg/dose/day ($10^9$ CFU/dose/day).

In the embodiment presented, during the use of the product for administering, the blister covering the two compartments 2 and 3 is removed.

The compartment 3 is then folded on the compartment 2 along a folding groove 6, thus causing the probiotics to adhere to the pharmaceutical film already impregnated with a phyto-estrogens. The film impregnated with phyto-estrogens and probiotics is then removed from the compartment that it occupies.

This film impregnated with the two active ingredients which then takes the form of a lubricated sheet, can then be introduced into the vagina.

The film disintegrates within the vagina, releasing these active ingredients in a targeted and efficient manner.

Such a film can be used to treat menopausal women for post-operational and pre-operational care or for the local treatment of trophic disorders of the vagina.

The invention claimed is:

1. A delivery device comprising:
   two distinct compartments (2, 3) shut by at least one lid, one (2) of said two distinct compartments containing a biodegradable film (4) for pharmaceutical or medicinal use for the topical delivery of at least one first active ingredient;
   wherein said at least one first active ingredient is deposited on, impregnated in, or incorporated with said biodegradable film; and
   the other (3) of said two distinct compartments containing at least one second active ingredient (5);
   wherein said two distinct compartments (2, 3) are intended to be folded one on top of the other after removal of said lid so that the at least one second active ingredient (5) is deposited on said biodegradable film (4);
   wherein said biodegradable film is made from a by-product of a soybean transformation process selected from the group consisting of okara, a permeate of soy milk ultra-filtration, or a combination thereof.

2. The delivery device according to claim 1, wherein the device is for gynecological use.

3. The delivery device according to claim 1, wherein said biodegradable film further comprises a film-forming agent.

4. The delivery device according to claim 3, wherein said film-forming agent is selected from the group consisting of caseinates and protein fractions from manufactured milk dairy products.

5. The delivery device according to claim 1 wherein said biodegradable film further comprises at least one plasticizer.

6. The delivery device according to claim 5 wherein said plasticizer is glycerol.

7. The delivery device according to claim 1 wherein said biodegradable film comprises:
   0% to 20% by weight of said okara;
   0% to 40% by weight of said permeate;
   5% to 60% by weight of a plasticizer;
   20% to 90% by weight of a film-forming agent; and
   0% to 20% by weight of water.

8. The delivery device according to claim 1, wherein said biodegradable film is intended to be applied to a mucous membrane.

9. The delivery device according to claim 8, wherein said biodegradable film is intended to be applied to the lips or to the inside of the mouth.

10. The delivery device according to claim 8, wherein said biodegradable film, is intended to be applied to the vulva or in the vagina.

11. The delivery device according to claim 1, wherein the at least one first or second active ingredient is an estrogen or a pseudo-estrogen.

12. The delivery device according to claim 11, wherein the at least one first or second active ingredient is contained in an extract of soybeans.

13. The delivery device according to claim 12 wherein the at least one first or second active ingredient includes a mixture of daidzin and genistin.

14. The delivery device according to claim 1, wherein the at least one first or second active ingredient is a probiotic.

* * * * *